United States Patent
Schafer et al.

(10) Patent No.: US 8,716,252 B2
(45) Date of Patent: May 6, 2014

(54) (METHYLSULFONYL) ETHYL BENZENE ISOINDOLINE DERIVATIVES AND THEIR PHARMACEUTICAL USES

(75) Inventors: Peter H. Schafer, Somerset, NJ (US); Anthony J. Frank, Easton, PA (US); Hon-Wah Man, Princeton, NJ (US); Sai L. Shankar, Chesterfield, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/518,843

(22) PCT Filed: Dec. 21, 2010

(86) PCT No.: PCT/US2010/061420
§ 371 (c)(1), (2), (4) Date: Aug. 21, 2012

(87) PCT Pub. No.: WO2011/079091
PCT Pub. Date: Jun. 30, 2011

(65) Prior Publication Data
US 2013/0116204 A1    May 9, 2013

Related U.S. Application Data

(60) Provisional application No. 61/289,356, filed on Dec. 22, 2009.

(51) Int. Cl.
*A61K 31/70* (2006.01)
*A61K 31/40* (2006.01)
*C07H 17/02* (2006.01)
*C07D 209/46* (2006.01)

(52) U.S. Cl.
USPC ............. 514/27; 514/416; 536/17.4; 548/472

(58) Field of Classification Search
None
See application file for complete search history.

(56) References Cited

U.S. PATENT DOCUMENTS 6,667,316 B1 * 12/2003 Man et al. ............... 514/323

FOREIGN PATENT DOCUMENTS

WO   WO 01/34606   5/2001

* cited by examiner

*Primary Examiner* — Traviss C McIntosh, III
(74) *Attorney, Agent, or Firm* — Jones Day

(57) ABSTRACT

Provided are (methylsulfonyl)ethyl benzene isoindoline compounds, and pharmaceutically acceptable salts, solvates, or stereoisomers thereof. Methods of use and pharmaceutical compositions of these compounds are also disclosed.

13 Claims, No Drawings

(METHYLSULFONYL) ETHYL BENZENE ISOINDOLINE DERIVATIVES AND THEIR PHARMACEUTICAL USES

This application is a §371 national stage application of PCT/US2010/061420, filed Dec. 21, 2010, which claims priority to U.S. Provisional Application No. 61/289,356, filed Dec. 22, 2009, both of which are incorporated herein by reference in their entireties.

1. FIELD

Provided herein are (methylsulfonyl)ethyl benzene isoindoline derivatives. Pharmaceutical compositions comprising the compounds and methods for treating, preventing and managing various disorders are also provided.

2. BACKGROUND

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNFα. Increased levels of cAMP also lead to the relaxation of airway smooth muscle. In addition, excessive or unregulated TNFα production has been implicated in a number of disease conditions including but not limited to autoimmune and inflammatory diseases. Specific disease conditions include endotoxemia and/or toxic shock syndrome [Tracey, et al., *Nature* 330, 662-664 (1987) and Hinshaw, et al., *Circ. Shock* 30, 279-292 (1990)], rheumatoid arthritis, inflammatory bowel disease, cachexia [Dezube, et al., *Lancet*, 335 (8690), 662 (1990)], lupus and cancer.

The primary cellular mechanism for the inactivation of cAMP is the breakdown of cAMP by a family of isoenzymes referred to as cyclic nucleotide phosphodiesterases (PDE) [Beavo and Reitsnyder, *Trends in Pharm.*, 11, 150-155, 1990]. There are greater than ten known members of the family of PDEs. It is well documented that the inhibition of PDE type IV (PDE 4) enzyme is particularly effective in both the inhibition of inflammatory mediator release and the relaxation of airway smooth muscle (Verghese, et al., *Journal of Pharmacology and Experimental Therapeutics*, 272(3), 1313-1320, 1995].

Increasing cAMP levels (e.g., inhibiting PDE 4) and/or thus decreasing TNFα levels constitutes a valuable therapeutic strategy for the treatment of many inflammatory, infectious, immunological, and malignant diseases. These include but are not restricted to: pulmonary diseases, septic shock, sepsis, endotoxic shock, hemodynamic shock and sepsis syndrome, post ischemic reperfusion injury, malaria, mycobacterial infection, meningitis, many types of psoriasis and other dermal diseases, congestive heart failure, fibrotic disease, cachexia, graft rejection, cancer, tumor growth, undesirable angiogenesis, autoimmune disease, opportunistic infections in AIDS, rheumatoid arthritis, rheumatoid spondylitis, osteoarthritis, other arthritic conditions, inflammatory bowel disease, Crohn's disease, ulcerative colitis, multiple sclerosis, systemic lupus erythematosis, ENL in leprosy, radiation damage, and hyperoxic alveolar injury.

In addition, a variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, tumor growth and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Accordingly, compounds that can control angiogenesis, inhibit PDE 4, and/or inhibit the production of certain cytokines, including TNFα, may be useful in the treatment and prevention of various diseases and conditions.

3. SUMMARY

Provided herein are (methylsulfonyl)ethyl benzene isoindoline analogs, and pharmaceutically acceptable salts, solvates (e.g., hydrates), prodrugs, clathrates, or stereoisomers thereof.

Also provided are methods of treating and managing various diseases or disorders. The methods comprise administering to a patient in need of such treatment or management, or having such a disease or disorder, a therapeutically effective amount of a compound provided herein, or a pharmaceutically acceptable salt, solvate, prodrug, clathrate, or stereoisomer thereof.

Also provided herein are methods of preventing various diseases and disorders, which comprise administering to a patient in need of such prevention, or at a risk of such a disease or disorder, a prophylactically effective amount of a compound provided herein, or a pharmaceutically acceptable salt, solvate, prodrug, clathrate, or stereoisomer thereof.

Also provided herein are pharmaceutical compositions, single unit dosage forms, dosing regimens and kits which comprise a compound provided herein, or a pharmaceutically acceptable salt, solvate, prodrug, clathrate, or stereoisomer thereof.

4. DETAILED DESCRIPTION

In one embodiment, provided are (methylsulfonyl)ethyl benzene isoindoline compounds, and pharmaceutically acceptable salts, solvates, prodrugs, clathrate, and stereoisomers thereof.

In another embodiment, provided are methods of treating, managing, and preventing various diseases and disorders, which comprises administering to a patient a therapeutically or prophylactically effective amount of a compound provided herein, or a pharmaceutically acceptable salt, solvate, prodrug, clathrate, or stereoisomer thereof. Examples of diseases and disorders are described herein.

In other embodiments, a compound provided herein, or a pharmaceutically acceptable salt, solvate, prodrug, clathrate, or stereoisomer thereof, is administered in combination with another drug ("second active agent") or treatment. Second active agents include small molecules and large molecules (e.g., proteins and antibodies), examples of which are provided herein, as well as stem cells. Methods, or therapies, that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable salt, solvate, prodrug, clathrate, or stereoisomer thereof, and optionally a second active agent.

4.1 Compounds

In one embodiment, provided herein is a compound of formula (I):

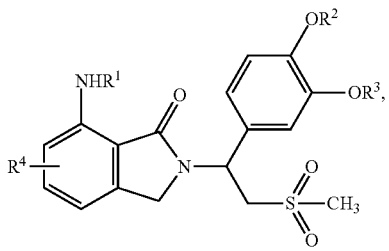

or a pharmaceutically acceptable salt, solvate, or stereoisomer thereof, wherein:

$R^1$ is hydrogen, glucuronide ("gluc"), or (cyclopropyl)-C(O)—, wherein the cyclopropyl may be substituted with one or more hydroxyl groups;

$R^2$ is hydrogen, methyl, or gluc;

$R^3$ is hydrogen, ethyl, or gluc; and $R^4$ is hydrogen, hydroxyl, or —O-gluc; with the proviso that when $R^2$ is methyl and $R^3$ is ethyl, then $R^1$ cannot be unsubstituted (cyclopropyl)-O—.

In one embodiment, $R^1$ is hydrogen. In another embodiment, $R^1$ is gluc. In another embodiment, $R^1$ is (cyclopropyl)-C(O)—. In another embodiment, $R^1$ is (cyclopropyl)-C(O)—, wherein the cyclopropyl is substituted with a hydroxyl group.

In one embodiment, $R^2$ is hydrogen. In another embodiment, $R^2$ is methyl. In another embodiment, $R^2$ is gluc.

In one embodiment, $R^3$ is hydrogen. In another embodiment, $R^3$ is ethyl. In another embodiment, $R^3$ is gluc.

In one embodiment, $R^4$ is hydroxyl. In another embodiment, $R^4$ is —O-gluc.

Each of the combinations resulting from $R^1$-$R^4$ is also provided herein.

In one embodiment, $R^1$ is hydrogen, $R^2$ is methyl, and $R^3$ is ethyl.

In another embodiment, $R^1$ is hydrogen, $R^2$ is gluc, and $R^3$ is ethyl.

In another embodiment, $R^1$ is (cyclopropyl)-C(O)— wherein the cyclopropyl is substituted with an —OH, $R^2$ is methyl, and $R^3$ is ethyl.

In another embodiment, $R^1$ is (cyclopropyl)-C(O)— and $R^3$ is ethyl. In another embodiment where $R^1$ is (cyclopropyl)-C(O)— and $R^3$ is ethyl, $R^2$ is hydrogen. In another embodiment where $R^1$ is (cyclopropyl)-C(O)— and $R^3$ is ethyl, $R^2$ is gluc.

In one embodiment, $R^2$ and $R^3$ are both hydrogen. In another embodiment where $R^2$ and $R^3$ are both hydrogen, $R^1$ is (cyclopropyl)-C(O)—.

In another embodiment, $R^1$ is (cyclopropyl)-C(O)— and $R^2$ is methyl. In another embodiment where $R^1$ is (cyclopropyl)-C(O)— and $R^2$ is methyl, $R^1$ is hydrogen. In another embodiment where $R^1$ is (cyclopropyl)-C(O)— and $R^2$ is methyl, $R^1$ is gluc.

In another embodiment, $R^1$ is (cyclopropyl)-C(O)—, wherein cyclopropyl is substituted with an —OH, and $R^3$ is ethyl. In another embodiment where $R^1$ is (OH-substituted cyclopropyl)-C(O)— and $R^3$ is ethyl, $R^2$ is hydrogen. In another embodiment where $R^1$ is (OH-substituted cyclopropyl)-C(O)— and $R^3$ is ethyl, $R^2$ is gluc.

Specific compounds include, but are not limited to:

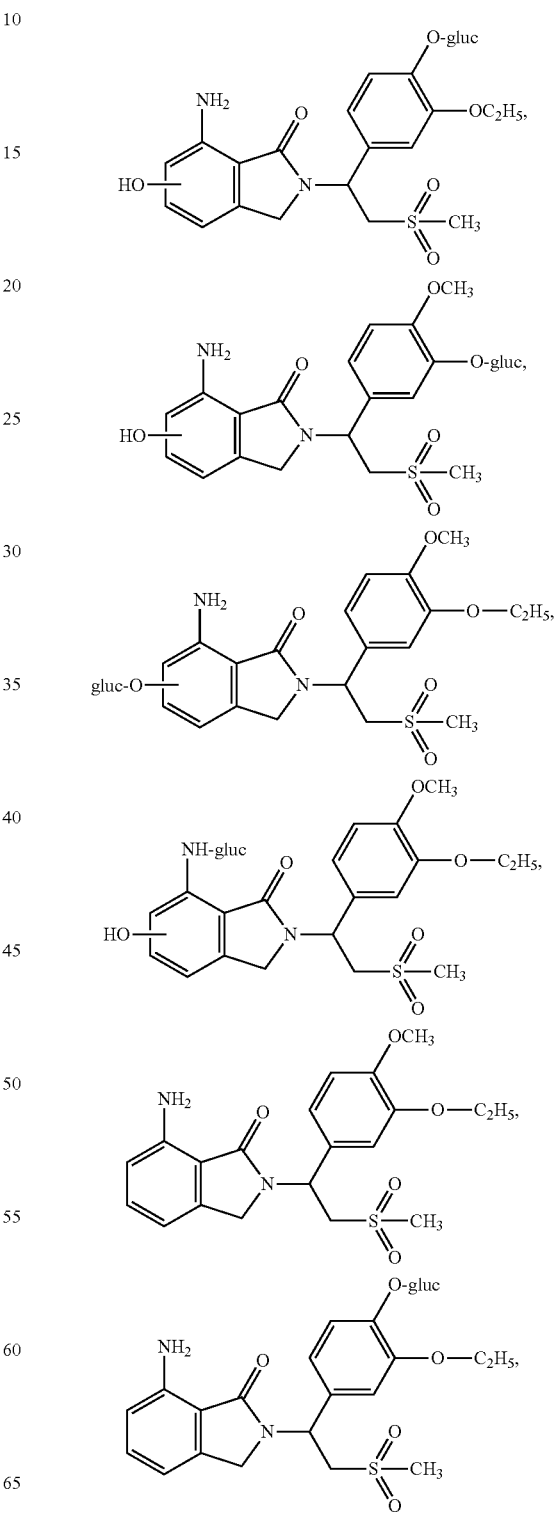

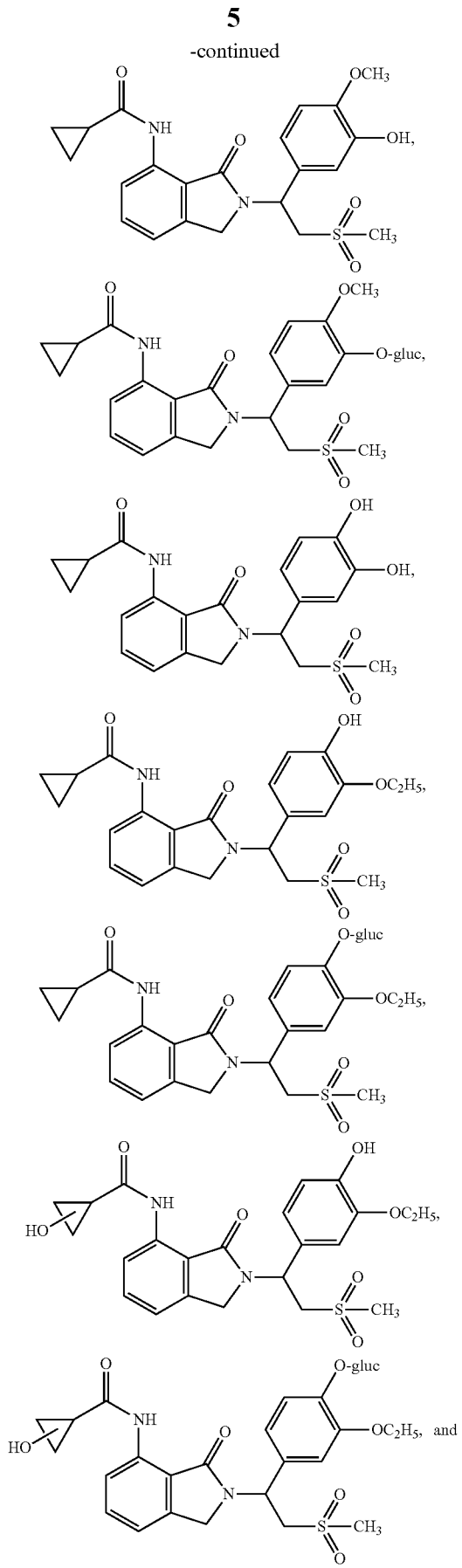

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In one embodiment, suitable are hydrochloric, hydrobromic, phosphoric, and sulfuric acids.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elselvier, N.Y. 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, carbamates that include lower alkylamine, substituted ethylenediamine, aminoacid, hydroxyalkylamine, heterocyclic and heteroaromatic amine, and polyether amine moieties.

As used herein, and unless otherwise specified, the term "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

As used herein, and unless otherwise indicated, the term "alkyl" refers to a saturated straight chain or branched hydrocarbon having a number of carbon atoms as specified herein. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The term "alkyl" also encompasses cycloalkyl.

As used herein, and unless otherwise specified, the term "cycloalkyl" means a specie of alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group is a monocyclic ring or bicyclic ring. Representative aryl groups include phenyl, anthracenyl, fluorenyl, indenyl, azulenyl, phenanthrenyl and naphthyl.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Methods of Treatment, Prevention and Management

Provided herein are methods of treating, preventing, and/or managing various diseases or disorders using a compound provided herein, or a pharmaceutically acceptable salt, solvate (e.g., hydrate), prodrug, clathrate, or stereoisomer thereof. Without being limited by a particular theory, compounds provided herein can inhibit PDE 4 enzymatic activity, control angiogenesis or inhibit the production of certain cytokines including, but not limited to, TNF-α, INF-α, IP-10, MIG, IL-1β, IL-12, IL-18, GM-CSF, and/or IL-6. Without being limited by a particular theory, compounds provided herein can stimulate the production of cetain other cytokines including IL-10, and also act as inhibitors of T cell activation, resulting in decreased production of cytokines such as, but not limited to, IL-2 and/or IFN-γ. In addition, compounds provided herein can inhibit the effects of NK cells. Further, compounds provided herein may be immunomodulatory and/or cytotoxic, and thus, may be useful as chemotherapeutic agents, in particular against diseases such as, but not limited to, chronic lymphocytic leukemia, acute lymphoblastic leukemia, and diffuse large B cell lymphoma. Compounds provided herein can also be anti-angiogenic, and thus, may be useful for the treatment of cancer. Consequently, without being limited by a particular theory, some or all of such characteristics possessed by the compounds provided herein may render them useful in treating, managing, and/or preventing various diseases or disorders.

Examples of diseases or disorders include, but are not limited to: pulmonary disorders including, but not limited to, asthma, COPD, scleroderma and idiopathic pulmonary fibrosis; skin diseases including, but not limited to, cutaneous lupus erythmatosus, discoid lupus erythmatosus, dermatomyositis, systemic lupus erythmatosus, psoriasis, atomic dermatitis, sarcoidosis and cutaneous sarcoidosis; TNFα related disorders including, but not limited to, inflammatory diseases, autoimmune diseases, rheumatoid arthritis, psoriatic arthritis, ankylosing spondylitis, gouty arthritis, psoriasis, Crohn's disease and ulcerative colitis; cancer; leukemia including chronic lymphocytic leukemia and acute lymphoblastic leukemia; lymphoma including diffuse large B cell lymphoma; disorders associated with angiogenesis such as cancer or tumor growth; pain including, but not limited to, Complex Regional Pain Syndrome ("CRPS"); Macular Degeneration ("MD") and uveitis and syndromes related thereof; asbestos-related disorders; parasitic diseases; immunodeficiency disorders; CNS disorders; CNS injury; atherosclerosis and related disorders; dysfunctional sleep and related disorders; hemoglobinopathy and related disorders (e.g., anemia); and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of reccurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "administration" encompasses provision of the compounds provided herein to a patient as they exist outside the body of the patient. The term therefore encompasses provision of an isolated or purified compound to a patient.

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: asthma; chronic obstructive pulmonary disease (COPD); primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; idiopathic pulmonary fibrosis; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

In one embodiment, provided herein are methods of treating, preventing or managing asthma. In another embodiment, provided herein are methods of treating, preventing or managing COPD. In another embodiment, provided herein are methods of treating, preventing or managing idiopathic pulmonary fibrosis.

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, wrinkles, and other skin diseases.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Other skin diseases include, but are not limited to, cutaneous lupus erythmatosus, discoid lupus erythmatosus, dermatomyositis, systemic lupus erythmatosus, psoriasis and cutaneous sarcoidosis. In one embodiment, provided herein are methods of treating, preventing or managing cutaneous lupus erythmatosus. In another embodiment, provided herein are methods of treating, preventing or managing discoid lupus erythmatosus. In another embodiment, provided herein are methods of treating, preventing or managing dermatomyositis. In another embodiment, provided herein are methods of treating, preventing or managing systemic lupus erythmatosus. In another embodiment, provided herein are methods of treating, preventing or managing psoriasis. In another embodiment, provided herein are methods of treating, preventing or managing cutaneous sarcoidosis.

Examples of elevated TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, gouty arthritis, rheumatoid spondylitis, ankylosing spondylitis, osteoarthritis, psoriatic arthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, fever, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In one embodiment, provided herein are methods of treating, preventing or managing rheumatoid arthritis. In another embodiment, provided herein are methods of treating, preventing or managing psoriatic arthritis. In another embodiment, provided herein are methods of treating, preventing or managing ankylosing spondylitis. In another embodiment, provided herein are methods of treating, preventing or managing gouty arthritis. In another embodiment, provided herein are methods of treating, preventing or managing Crohn's disease. In another embodiment, provided herein are methods of treating, preventing or managing ulcerative colitis. In another embodiment, provided herein are methods of treating, preventing or managing psoriasis.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one embodiment, provided herein are methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow. In one embodiment, provided herein are methods of treating, preventing or managing chronic lymphocytic leukemia. In another embodiment, provided herein are methods of treating, preventing or managing acute lymphoblastic leukemia.

In another embodiment, provided herein are methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract.

Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), diffuse large B cell lymphoma, centrocytic lymphoma, diffuse small-cleaved cell lymphoma (DSCCL), follicular lymphoma, and any type of the mantle cell lymphomas that can be seen under the microscope (nodular, diffuse, blastic and mentle zone lymphoma). In one embodiment, provided herein are methods of treating, preventing or managing diffuse large B cell lymphoma.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, cancer and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and uveitis and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE). In one embodiment, provided herein are methods of treating, preventing or managing uveitis.

Examples of asbestos-related disorders include, but are not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Banesia Gibsoni, Besnoitia darlingi, Cytauxzoon felis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. publication no. 2006/0188475, published Aug. 24, 2006. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

| Artery | Body Areas Supplied |
|---|---|
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

In other embodiments, the use of compounds provided herein in various immunological applications, in particular, as vaccine adjuvants, particularly anticancer vaccine adjuvants, as disclosed in U.S. Publication No. 2007/0048327, published Mar. 1, 2007, which is incorporated herein in its entirety by reference, is also encompassed. These embodiments also relate to the uses of compounds provided herein in combination with vaccines to treat or prevent cancer or infectious diseases, and other various uses of immunomodulatory compounds such as reduction or desensitization of allergic reactions.

Doses of a compound provided herein, or a pharmaceutically acceptable salt, solvate, clathrate, stereoisomer or prodrug thereof, vary depending on factors such as: specific indication to be treated, prevented, or managed; age and condition of a patient; and amount of second active agent used, if any. Generally, a compound provided herein, or a pharmaceutically acceptable salt, solvate, clathrate, stereoisomer or prodrug thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, from about 1 mg to about 30 mg, or from about 1 mg to about 20 mg.

4.3 Second Active Agents

A compound provided herein, or a pharmaceutically acceptable salt, solvate, prodrug, clathrate, or stereoisomer thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or a pharmaceutically acceptable salt, solvate, clathrate, stereoisomer or prodrug thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); monoclonal antibodies (such as, for example, rituximab (Rituxae), tositumomab (Bexxae), edrecolomab (Panorex) and G250); and anti-TNF-α antibodies. Examples of small molecule active agents include, but are not limited to, anticancer agents and antibiotics (e.g., clarithromycin). Specific second active compounds that can be combined with compounds provided herein vary depending on the specific indication to be treated, prevented or managed.

In some embodiments, the second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, steroids and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

In some embodiments, the second active agents include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

In other embodiments, the second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B;

velaresol; veramine; verdins; verteporfin; vinorelbine; vinxaltine; vitaxin; vorozole; zanoterone; zeniplatin; zilascorb; and zinostatin stimalamer.

In some embodiments, the active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadroe), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, etoposide, and various cytotoxic and/or cytostatic agents.

In some embodiments, examples of specific second agents according to the indications to be treated, prevented, or managed can be found in the following references, all of which are incorporated herein in their entireties: U.S. Pat. Nos. 6,281,230 and 5,635,517; and U.S. publication nos. 2004/0220144, 2004/0190609, 2004/0087546, 2005/0203142, 2004/0091455, 2005/0100529, 2005/0214328, 2005/0239842, 2006/0154880, 2006/0188475, 2006/0122228, and 2005/0143344.

In some embodiments, the second active agents include, but are not limited to, antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, NSAIDs and other therapeutics found, for example, in the *Physician's Desk Reference* 2003. Specific examples include, but are not limited to, salicylic acid acetate (Aspirin®), celecoxib (Celebrex®), Enbrel®, ketamine, ibuprofen, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Aculae), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

In some embodiments, the second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16,17-1-methylethylidinebis (oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited herein are incorporated in their entireties by reference.

In some embodiments, the second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

In some embodiments, the second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interferon gamma, itraconazole, a combination of dead promastigotes and BCG, leucovorin, corticosteroids, sulfonamide, spiramycin, IgG (serology), trimethoprim, and sulfamethoxazole.

In some embodiments, the second active agents, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

In some embodiments, the second active agents include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetyleucine monoethanolamine, lalizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

In some embodiments, the second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

In some embodiments, the second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

In some embodiments, the second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-nl, interferon alfa-n3, interferon beta-I a, and interferon gamma-I b; and G-CSF; hydroxyurea; butyrates or butyrate derivatives; nitrous oxide; hydroxy urea; HEMOXINT™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a compound provided herein, or a pharmaceutically acceptable salt, solvate, clathrate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., *Physicians' Desk Reference* (60$^{th}$ ed., 2006).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

4.4 Cycling Therapy

In certain embodiments, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

4.5 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed in Section 4.3, above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences,* 18th ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

4.5.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

4.5.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

4.5.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences*, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

4.6 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 (2S,3S,4S,5R,6R)-6-(2-(2-((S)-1-(3-ethoxy-4-methoxyphenyl)-2-(methylsulfonyl)ethyl)-1,3-dioxoisoindolin-4-yl-amino)-2-oxoethoxy)-3,4,5-trihydroxytetrahydro-2H-pyran-2-carboxylic Acid

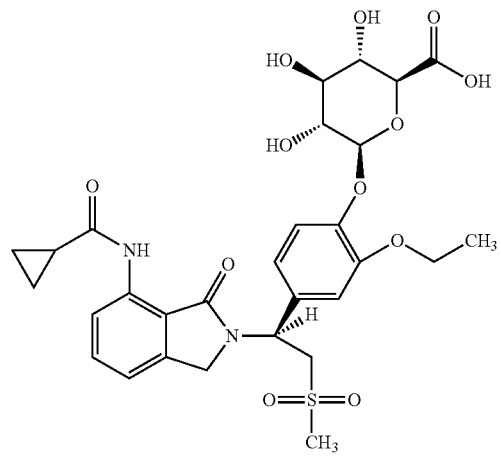 [SMILES: CCOc1cc([C@@H](CS(C)(=O)=O)N2Cc3cccc(NC(=O)C4CC4)c3C2=O)ccc1O[C@@H]1O[C@H](C(=O)O)[C@@H](O)[C@H](O)[C@H]1O]

Step 1: A reaction mixture of (S)—N-(2-(1-(3-ethoxy-4-hydroxyphenyl)-2-(methylsulfonyl)ethyl)-3-oxoisoindolin-4-yl)cyclopropanecarboxamide (0.38 g, 0.83 mmol) and 3,4,5-triacetoxy-6-(2,2,2-trichloro-acetimidoyloxy)-tetrahydropyran-2-carboxylic acid benzyl ester (0.46 g, 0.83 mmol) in dichloromethane (40 mL) was chilled to $-15°$ C. to $-20°$ C., treated with $BF_3.OEt_2$ (0.10 mL, 0.83 mmol), and stirred for 2 hours at $-15°$ C. to $-20°$ C. After 2 hours, the reaction mixture was then allowed to warm to room temperature and stirred overnight. The reaction mixture was diluted with EtOAc (10 vol) then washed with saturated aqueous $NaHCO_3$ (5 vol), 2% NaCl (5 vol), dried ($MgSO_4$), and concentrated. The crude mixture was eluted through a 120 g ISCO column, 5% to 20% EtOAc/$CH_2Cl_2$. After concentration of the fractions, the product was dried under vacuum for 12 hours, which afforded (2S,3S,4S,5R,6S)-2-(benzyloxycarbonyl)-6-(4-((S)-1-(7-(cyclopropanecarboxamido)-1-oxoisoindolin-2-yl)-2-(methylsulfonyl)ethyl)-2-ethoxyphenoxy)tetrahydro-2H-pyran-3,4,5-triyl triacetate (250 mg, 56% yield) as a light yellow solid: $^1$H-NMR (DMSO-$d_6$): 10.4 (s, 1H), 8.26-8.23 (d, J=8 Hz, 1H), 7.53-7.48 (t, J=7 Hz, 1H), 7.39-7.31 (m, 5H), 7.20-7.18 (d, J=7 Hz, 1H), 7.13-7.12 (d, J=2 Hz, 1H), 7.09-7.07 (d, J=9 Hz, 1H), 6.95-6.92 (dd, J=1.8 Hz, 1H), 5.9-5.88 (dd, J=4, 10 Hz, 1H), 5.44-5.37 (overlapping d and t, $J_d$=8 Hz, $J_t$=10 Hz, 2H), 5.17-5.03 (m, 4H), 4.70-4.63 (m, 2H), 4.38-4.30 (m, 1H), 4.21-4.15 (d, J=18 Hz, 1H), 4.08-3.95 (m, 3H), 3.04 (s, 3H), 2.00 (s, 3H), 1.97 (s, 3H), 1.81-1.76 (m, 4H), 1.32-1.27 (t, J=7 Hz, 3H), 0.89-0.86 (d, J=6 Hz, 4H). HPLC: Waters Nova-Pak C18 column, 150×3.9 mm, 4 µm; Gradient CH₃CN/0.1% aq H₃PO₄ 10/90 to 90/10 in 20 min, 1.0 mL/min, $t_R$ 14.022 min, 98.5 AP at 240 nm.

Step 2: A suspension of (2S,3S,4S,5R,6S)-2-(benzyloxycarbonyl)-6-(2-ethoxy-4-((S)-2-(methylsulfonyl)-1-(4-nitro-1,3-dioxoisoindolin-2-3/1) ethyl)phenoxy)tetrahydro-2H-pyran-3,4,5-triyl triacetate (1.67 g, 1.96 mmol) and 10% Pd—C (250 mg) in EtOAc (150 mL) was placed in a Parr hydrogenation bottle (purged 3× nitrogen, 3× hydrogen) and the pressure was adjusted to 40-45 psi. After 4 hours, the reaction mixture was filtered through Celite and the filter cake was washed with EtOAc (5 mL). After concentration, the product was dried at 40° C. under vacuum for 2 hours, which afforded (2S,3S,4S,5R,6S)-3,4,5-triacetoxy-6-(4-((S)-1-(7-(cyclopropanecarboxamido)-1-oxoisoindolin-2-yl)-2-(methylsulfonyl)ethyl)-2-ethoxyphenoxy)tetrahydro-2H-pyran-2-carboxylic acid as a light-yellow solid (1.45 g, >99% yield). ¹H-NMR (DMSO-d₆): 13.349 (s, 1H), 10.48 (s, 1H), 8.25-8.22 (d, J=8 Hz, 1H), 7.53-7.48 (t, J=7 Hz, 1H), 7.21-7.18 (d, J=7 Hz, 1H), 7.12-7.08 (m, 2H), 7.01-6.97 (dd, J=1.8 Hz, 1H), 5.9-5.85 (dd, J=4, 10 Hz, 1H), 5.44-5.37 (overlapping d and t, $J_d$=8 Hz, J=10 Hz, 2H), 5.13-5.04 (m, 2H), 4.69-4.63 (d, J=18 Hz, 1H), 4.51-4.48 (d, J=10 Hz, 1H), 4.38-4.29 (m, 1H), 4.21-4.15 (d, J=18 Hz, 1H), 4.08-3.99 (m, 3H), 3.04 (s, 3H), 2.01 (s, 3H), 1.98 (s, 3H), 1.97 (s, 3H), 1.82-1.76 (m, 1H), 1.35-1.30 (t, J=6 Hz, 3H), 0.89-0.86 (d, J=6 Hz, 4H). HPLC: Waters Nova-Pak C18 column, 150×3.9 mm, 4 µm; Gradient CH₃CN/0.1% aq H₃PO₄ 10/90 to 90/10 in 20 min, 1.0 mL/min, $t_R$ 10.951 min, 96.2 AP at 240 nm.

Step 3: A suspension of (2S,3S,4S,5R,6S)-3,4,5-triacetoxy-6-(4-((S)-1-(7-(cyclopropanecarboxamido)-1-oxoisoindolin-2-yl)-2-(methylsulfonyl)ethyl)-2-ethoxyphenoxy)tetrahydro-2H-pyran-2-carboxylic acid (1.4 g, 1.84 mmol) and Na₂CO₃ (0.59 g, 5.52 mmol) in MeOH (40 mL) was heated at 30° C. for 8 hours, followed by room temperature for 8 hours. The reaction mixture was cooled to 0° C.-5° C. then acidified with AcOH (0.53 mL). After warming the reaction mixture to room temperature, the mixture was concentrated. The crude residue was eluted through a PrepSep 10 g C18 column with 10 to 25% CH₃CN/H₂O. Lyophilization of the fractions yielded (2S,3S,4S,5R,6R)-6-(2-(2-((S)-1-(3-ethoxy-4-methoxyphenyl)-2-(methylsulfonyl)ethyl)-1,3-dioxoisoindolin-4-ylamino)-2-oxoethoxy)-3,4,5-trihydroxytetrahydro-2H-pyran-2-carboxylic acid as a light-yellow solid (920 mg, 78%): ¹H-NMR (MeOH-d₆): 8.29-8.26 (d, J=8.4 Hz, 1H), 7.76-7.71 (t, J=8.0 Hz, 1H), 7.49-7.43 (t, J=7.0 Hz, 1Hv), 7.27-7.25 (d, J=8 Hz, 2H), 7.15-7.09 (m, 2 Hz), 7.04-7.01 (dd, J=2, 9 Hz, 1H), 6.06-6.01 (dd, J=4.0, 11.0 Hz, 1H), 4.95-4.93 (d, J=7 Hz, 1H), 4.87 (bs, exchangeable protons, 5H), 4.64-4.58 (d, J=18 Hz, 1H), 4.33-4.24 (m, 1H), 4.19-4.07 (m, 3H), 3.8 (s, 3H), 3.96-3.90 (dd, J=4, 14 Hz, 1H), 3.77-3.74 (d, J=8 Hz, 1H), 3.59-3.51 (m, 3H), 3.06 (s, 3H), 1.82-1.75 (m, 1H), 1.42-1.38 (t, J=14 Hz, 3H), 1.05-0.92 (m, 4H). ¹³C-NMR (DMSO-d₆): 171.8, 171.7, 168.1, 148.3, 146.9, 142.2, 136.7, 132.9, 131.3, 119.9, 117.5, 117.0, 116.8, 116.7, 116.2, 113.7, 100.1, 76.7, 73.9, 73.0, 71.8, 64.5, 53.7, 48.8, 46.2, 40.9, 15.7, 15.4, 7.8. HPLC: Waters Nova-Pak C18 column, 150×3.9 mm, 4 µm; Gradient CH₃CN/0.1% aq H₃PO₄ 10/90 to 90/10 in 20 min, 1.0 mL/min, $t_R$ 6.952 min, 99.03 AP at 240 nm. Calcd for C₂₉H₃₄N₂O₁₂S 1.9[H₂O]: % C (52.07); % H (5.70); % N (4.19). Found: % C (51.78); % H (5.30); % N (4.01).

5.2 (S)—N-(2-(1-(3-ethoxy-4-hydroxyphenyl)-2-(methylsulfonyl)ethyl)-3-oxosoindolin-4-yl)cyclopropanecarboxamide

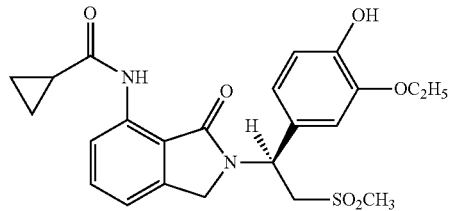 [SMILES: CCOc1cc([C@@H](CS(C)(=O)=O)N2Cc3cccc(NC(=O)C4CC4)c3C2=O)ccc1O]

Step 1: A mixture of (S)-7-amino-2-(1-(3-ethoxy-4-methoxyphenyl)-2-(methylsulfonyl)ethyl)isoindolin-1-one (10 g, 24.7 mmol) and neat TMSI (50 g, 250 mmol) was heated at 80° C. for 1.5 to 2 hours. The mixture was cooled to 0° C.-5° C. and quenched with 5% aqueous sodium sulfite. Methylene chloride (CH₂Cl₂) was added, and the slurry stirred vigorously until all the solids dissolved. The CH₂Cl₂ layer was separated and washed with water and brine, then concentrated to a foam (9.6 g, >99% yield). The crude material was purified by column chromatography (MeOH 0-5%/CH₂Cl₂ over 60 mins). The desired fractions were combined and concentrated to give (S)-7-amino-2-(1-(3-ethoxy-4-hydroxyphenyl)-2-(methylsulfonyl)ethyl)isoindolin-1-one as a yellow solid (6 g, 62% yield). UPLC: Acquity UPLC BEH C8, 2.1×50 mm, 1.7µ, 99:1 to 15:85 over 2 minutes gradient, 0.1% aq. TFA/MeCN, 0.8 mL/min, 35° C.: $t_R$ 0.86 minute.

Step 2: To a mixture of (S)-7-amino-2-(1-(3-ethoxy-4-hydroxyphenyl)-2-(methylsulfonyl)ethyl)isoindolin-1-one (5.86 g, 15.0 mol) in THF (60 mL) was added cyclopropanecarbonyl chloride (1.5 mL, 16.1 mmol). The mixture was heated to 60° C. for 1 hour then cooled to room temperature. The solvent was removed and the crude residue purified using column chromatography (MeOH/CH₂Cl₂; 0-5% over 60 minutes) to give 4.7 g of crude, 68% yield. Further purification was then carried out by prep-HPLC to give (S)—N-(2-(1-(3-ethoxy-4-hydroxyphenyl)-2-(methylsulfonyl)ethyl)-3-oxoisoindolin-4-yl)cyclopropanecarboxamide as a white solid (1.38 g, 20% yield). HPLC: HPLC: Hypersil DBS C8 column, 250×4.6 mm, 5 µm; 99/1 to 85/15 over 15 min Gradient CH₃CN/10 mM aq. KH₂PO₄, 1.0 mL/min, 35° C., run time 20 minutes: $t_R$ 12.45 minutes. ¹H-NMR (DMSO-d₆): 10.51 (1H, s), 9.07 (1H, s), 8.22-8.25 (1H, d), 7.47-7.53 (1H, t), 7.18-7.20 (1H, d), 7.01 (1H, d), 6.78-6.86 (2H, m), 5.82-5.87 (1H, m), 4.61-4.67 (1H, d), 3.91-4.33 (5H, m), 3.02 (3H, s), 1.76-1.82 (1H, m), 1.31-1.36 (3H, t), 0.82-0.96 (4H, m); LC-MS ES⁺ (M+1) 459.

5.3 (S)—N-(2-(1-(3,4-dihydroxyphenyl)-2-(methylsulfonyl)ethyl)-3-oxosoindolin-4-yl)cyclopropane carboxamide

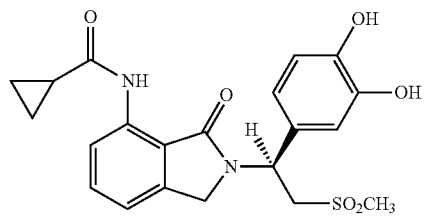 [SMILES: CS(=O)(=O)C[C@H](c1ccc(O)c(O)c1)N1Cc2cccc(NC(=O)C3CC3)c2C1=O]

A mixture of (S)-7-amino-2-(1-(3-ethoxy-4-methoxyphenyl)-2-(methylsulfonyl) ethyl)isoindolin-1-one (5 g, 12.4 mmol) and neat TMSI (25 g, 125 mmol) was heated at 80° C. for 16 hours. The mixture was cooled to room temperature and quenched with 5% aq. sodium sulfite. Ethyl acetate was added and the layers were separated. The organic layer was washed with water, brine and then dried over Na$_2$SO$_4$. The organic layer was concentrated, followed by a solvent swap to THF. To the THF solution, was added cyclopropanecarbonyl chloride (1.2 mL, 13.2 mmol). The mixture was heated to 40° C. for 0.5 hour then cooled to room temperature. The mixture was quenched with 1 N aq. NaHCO$_3$ then extracted with ethyl acetate. The organic was washed with 1 N aq. NaHCO$_3$, water, then brine. The solvent was removed and the crude was suspended in ACN at 40° C. for 1 hour. The product was collected by filtration to give 1 g of crude, 19% yield. Further purification by prep-HPLC followed by treatment with 2 N aq. HCl gave (S)—N-(2-(1-(3,4-dihydroxyphenyl)-2-(methylsulfonyl)ethyl)-3-oxoisoindolin-4-yl)cyclopropanecarboxamide as a white solid (0.25 g, 5% yield). HPLC: HPLC: Hypersil DBS C8 column, 250×4.6 mm, 5 μm; 99/1 to 85/15 over 15 minutes Gradient CH$_3$CN/10 mM aq. KH$_2$PO$_4$, 1.0 mL/min, 35° C., run time 20 minutes: t$_R$ 10.91 minutes. $^1$H-NMR (DMSO-d$_6$): 10.51 (1H, s), 9.02-9.07 (2H, d), 8.22-8.25 (1H, d), 7.48-7.53 (1H, t), 7.18-7.20 (1H, d), 6.70-6.78 (3H, m), 5.77-5.81 (1H, m), 4.59-4.65 (1H, d), 3.86-4.26 (3H, m), 3.02 (3H, s), 1.76-1.83 (1H, m), 0.88-0.90 (4H, m). LC-MS ES$^+$ (M+1) 431.

5.4 (S)—N-(2-(1-(3-hydroxy-4-methoxyphenyl)-2-(methylsulfonyl)ethyl)-3-oxoisoindolin-4-yl)cyclopropanecarboxamide

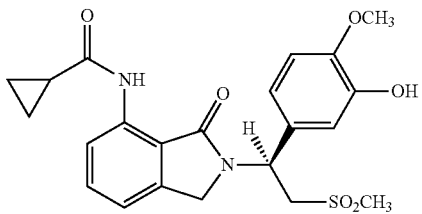 [SMILES: COc1ccc([C@@H](CS(C)(=O)=O)N2Cc3cccc(NC(=O)C4CC4)c3C2=O)cc1O]

Step 1: A mixture of (S)-7-amino-2-(1-(3-ethoxy-4-methoxyphenyl)-2-(methylsulfonyl)ethyl)isoindolin-1-one (10 g, 24.7 mmol) and neat TMSI (50 g, 250 mmol) was heated at 80° C. for 1.5 to 2 hours. The mixture was cooled to 0° C.-5° C. and quenched with 5% aq. sodium sulfite. Methylene chloride was added, and the slurry stirred vigorously until all the solids dissolved. The CH$_2$Cl$_2$ layer was separated and washed with water and brine, then concentrated to a foam (9.6 g, >99% yield). The crude material was purified by column chromatography (MeOH 0-5%/CH$_2$Cl$_2$ over 60 minutes). The desired fractions were combined and concentrated to give (S)-7-amino-2-(1-(3-hydroxy-4-methoxyphenyl)-2-(methylsulfonyl)ethyl)isoindolin-1-one as a yellow solid (6 g, 65% yield). UPLC: Acquity UPLC BEH C8, 2.1×50 mm, 1.7μ, 99:1 to 15:85 over 2 minutes gradient, 0.1% aq. TFA/MeCN, 0.8 mL/min, 35° C.: t$_R$ 0.80 minutes.

Step 2: To a mixture of (S)-7-amino-2-(1-(3-hydroxy-4-methoxyphenyl)-2-(methylsulfonyl)ethyl)isoindolin-1-one (5.86 g, 15.6 mmol) in THF (60 mL), was added cyclopropanecarbonyl chloride (1.5 mL, 16.1 mmol). The mixture was heated to 60° C. for 1 hour then cooled to room temperature. The solvent was removed and the crude residue purified using column chromatography (MeOH/CH$_2$Cl$_2$: 0-5% over 60 minutes) to give 4.7 g of crude, 68% yield. Further purification was then carried out by prep-HPLC to give (S)—N-(2-(1-(3-hydroxy-4-methoxyphenyl)-2-(methylsulfonyl)ethyl)-3-oxoisoindolin-4-yl)cyclopropanecarboxamide as a white solid (0.3 g, 4.3% yield). HPLC: HPLC: Hypersil DBS C8 column, 250×4.6 mm, 5 μm; 99/1 to 85/15 over 15 minutes Gradient CH$_3$CN/10 mM aq. KH$_2$PO$_4$, 1.0 mL/min, 35° C., run time 20 minutes: t$_R$ 11.84 minutes. $^1$H-NMR (DMSO-d$_6$): 10.50 (1H, s), 9.11 (1H, s), 8.22-825 (1H, d), 7.48-7.53 (1H, t), 7.18-7.2 (1H, d), 6.84-6.95 (3H, m), 5.80-5.85 (1H, m), 4.60-6.66 (1H, d), 3.90-4.30 (3H, m), 3.75 (3H, s), 3.04 (3H, s), 1.79-1.83 (1H, m), 0.88-0.90 (4H, m); LC-MS ES$^+$ (M+1) 445.

5.5 7-amino-2-[(1S)-1-(3-ethoxy-4-methoxy-phenyl)-2-methanesulfonyl-ethyl]-2,3-dihydro-isoindol-1-one

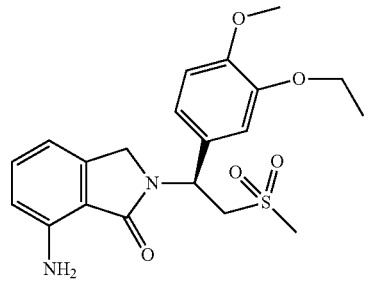 [SMILES: CCOc1cc([C@@H](CS(C)(=O)=O)N2Cc3cccc(N)c3C2=O)ccc1OC]

Step 1: A solution of 2-bromomethyl-6-nitro-benzoic acid methyl ester (4.0 g, 14.6 mmol), (1S)-1-(3-ethoxy-4-methoxy-phenyl)-2-methanesulfonyl-ethylamine (4.0 g, 14.6 mmol) and triethylamine (4.4 mL, 31.6 mmol) in DMF (40 mL) was heated at 80° C.-90° C. for 1 day. The solvent was removed in vacuo to give an oil. The oil was extracted with ethyl acetate (150 mL) and HCl (2N, 50 mL). The organic layer was washed with HCl (2N, 2×50 mL), water (2×50 mL), brine (2×50 mL) and dried over MgSO$_4$. The solvent was removed in vacuo to give a yellow oil. The oil was slurried in ether (50 mL) to give a suspension. The suspension was filtered and washed with ether to give 2-[(1S)-1-(3-ethoxy-4-methoxy-phenyl)-2-methanesulfonyl-ethyl]-7-nitro-2,3-dihydro-isoindol-1-one as a yellow solid (3.43 g, 54% yield): $^1$H NMR (CDCl$_3$) δ 1.5 (t, J=7 Hz, 3H, CH$_3$), 2.99 (s, 3H, CH$_3$), 3.69 (dd, J=5, 15 Hz, 1H, CHH), 3.86 (s, 3H, CH$_3$), 4.07 (q, J=7 Hz, 2H, CH$_2$), 4.27 (dd, J=11, 15 Hz, 1H, CHH), 4.30 (d, J=17 Hz, 1H, NCHH), 4.54 (d, J=17 Hz, 1H, NCHH), 5.70 (dd, J=5, 10 Hz, 1H, NCH), 6.85 (d, J=8 Hz, 1H, Ar), 6.94-7.00 (m, 2H, Ar), 7.58-7.76 (m, 3H, Ar).

Step 2: A suspension of 2-[(1S)-1-(3-ethoxy-4-methoxy-phenyl)-2-methanesulfonyl-ethyl]-7-nitro-2,3-dihydro-isoindol-1-one (3.0 g, 6.9 mmol) and Pd/C (10% 350 mg) in methanol/ethyl acetate (150 mL each) was shaken under hydrogen (50-60 psi) in a Parr for 20 hours. The suspension was filtered thru a pad of Celite, and washed with acetone (300 mL). The solvent was removed in vacuo to give a solid. The solid was slurried in methanol (10 mL) for 3 hours. The suspension was filtered and washed with methanol to give 7-amino-2-[(1S)-1-(3-ethoxy-4-methoxy-phenyl)-2-methanesulfonyl-ethyl]-2,3-dihydro-isoindol-1-one as a white solid (1.5 g, 55% yield): mp, 135-137° C.; $^1$H NMR (CDCl$_3$) δ 1.44 (t, J=7 Hz, 3H, CH$_3$), 2.93 (s, 3H, CH$_3$), 3.66 (dd, J=5, 15 Hz, 1H, CHH), 3.85 (s, 3H, CH$_3$), 4.06 (q, J=7 Hz, 2H, CH$_2$), 4.13 (d, J=16 Hz, 1H, CHH), 4.22 (dd, J=10, 15 Hz, 1H, CHH), 4.35 (d, J=17 Hz, 1H, CHH), 5.19 (brs, 2H, NH$_2$), 5.64 (dd, J=5, 10 Hz, 1H, NCH), 6.54 (d, J=8 Hz, 1H, Ar), 6.61 (d, J=7 Hz, 1H, Ar), 6.83 (d, J=8 Hz, 1H, Ar), 6.90-6.96 (m, 2H, Ar), 7.20 (t, J=8 Hz, 1H, Ar); $^{13}$C NMR (CDCl$_3$) δ 14.59, 41.28, 48.01, 51.81, 55.87, 56.14, 64.48, 110.98, 111.38, 112.22, 113.41, 114.75, 119.23, 129.89, 133.08, 142.36, 146.02, 148.72, 149.45, 170.57; Anal Calcd for C$_{20}$H$_{24}$N$_2$O$_5$S: C, 59.39; H, 5.98; N, 6.93. Found: C, 59.04; H, 6.04; N, 6.74.

5.6 Assays 5.6.1 PDE 4 Inhibition Assay

PDE 4 inhibition may be assays using any methods conventionally known in the art. For example, using a modification of the method of Hill and Mitchell [Hill and Mitchell, Faseb J., 8, A217 (1994)], U937 cells (a human promonocytic cell line) are grown to 1×10$^6$ cells/mL and collected by centrifugation. A cell pellet of 1×10$^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N$^1$,N$^1$-tetraacetic acid (EGTA), 1 μM phenylmethylsulfonyl fluoride (PMSF), and 1 μg/mL leupeptin). Cells are homogenized with 20 strokes in a Dounce homogenizer and the supernatant containing the cytosolic fraction are obtained by centrifugation. The supernatant is then loaded onto a Sephacryl S-200 column equilibrated in homogenization buffer. The crude phosphodiesterase type 4 enzyme is eluted in homogenization buffer at a rate of approximately 0.5 mL/min and fractions are assayed for phosphodiesterase activity using rolipram. Fractions containing PDE 4 activity (rolipram sensitive) are pooled and aliquoted for later use.

The phosphodiesterase assay is carried out based on the procedure described by Hill and Mitchell. The assay is carried out in a total volume of 100 μl containing various concentration of the compounds of interest, 50 mM Tris-HCl, pH 7.5, 5 mM magnesium chloride and 1 μM cAMP of which 1% is $^3$H cAMP. Reactions are incubated at 30° C. for 30 minutes and then terminated by boiling for 2 minutes. The amount of PDE 4 containing extract used for these experiments is predetermined such that reactions are within the linear range and consume less than 15% of the total substrate. Following termination of reaction, samples are chilled at 4° C. and then treated with 10 μl of 10 mg/mL snake venom for 15 minutes at 30° C. Unused substrate then is removed by adding 200 μl of a quaternary ammonium ion exchange resin (AG1-X8, BioRad) for 15 minutes. Samples then are spun at 3000 rpm for 5 minutes and 50 μl of the aqueous phase are taken for counting. Each data point is carried out in duplicate and activity is expressed as percentage of control. The IC$_{50}$s of the compounds are then determined from dose response curves of a minimum of three independent experiments.

5.6.2 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 μg/ml streptomycin (Life Technologies).

PBMC (2×10$^5$ cells) are plated in 96-well flat-bottom Costar tissue culture plates (Corning, N.Y., USA) in triplicate. Cells are stimulated with LPS (from *Salmonella abortus* equi, Sigma cat. no. L-1887, St. Louis, Mo., USA) at 1 ng/ml final in the absence or presence of compounds. Compounds provided herein are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% CO$_2$, and supernatants are then collected, diluted with culture medium and assayed for TNFα levels by ELISA (Endogen, Boston, Mass., USA). IC$_{50}$s are calculated using non-linear regression, sigmoidal dose-response, constraining the top to 100% and bottom to 0%, allowing variable slope (GraphPad Prism v3.02).

5.6.3 Various PDE 4 Inhibition Related Assays 5.6.3.1 PBMC Purification and Stimulation Human leukocytes units from healthy blood donors (Blood Center of New Jersey, East Orange, N.J.) are diluted 1:1 with sterile Hank's Balanced Salt Solution (HBSS) and centrifuged over room temperature Ficoll-Paque Plus (GE Healthcare) to yield peripheral blood mononuclear cells (PBMC). PBMC are washed in HBSS and resuspended in Roswell Park Memorial Institute (RPMI) complete medium (RPMI 1640, BioWhittaker, Walkersville, Md.), 5% human serum, 100 U/ml penicillin, 100 mg/ml streptomycin, 2 mM L-glutamine) and counted. One hundred μl (2×10$^6$/ml) of PBMC are added to each well of a 96 well flat-bottom plate (final cell count=2×10$^5$/well) and incubated at 37° C. for 1 hour. Fifty ml (4×) compound is added to each test well and 50 ml medium containing 1% dimethylsulfoxide (DMSO) is added to each control well ([DMSO]$_{final}$=0.25%). The plate is incubated for 1 hour at 37° C. Cells are then stimulated with 50 μl of 4 ng/ml lipopolysaccharide (LPS) from *Salmonella abortus equii* (Sigma) ([LPS]$_{final}$=1 ng/ml) and incubated for 18 hours at 37° C. For stimulation with superantigen, PBMC are plated in 96-well tissue culture plates at 3×10$^5$ cells/well in complete medium, pretreated with compounds at 37° C. for 1 hour, then stimulated with 100 ng/ml Staphylococcal enterotoxin B (SEB) (Toxin Technology, Sarasota, Fla.) for 18 hours.

5.6.3.2 Quantitative Reverse Transcription-Polymerase Chain Reaction

Cells are harvested and RNA isolation is performed according to manufacturer's instructions (e.g., RNeasy, Qiagen, Valencia, Calif.). Reverse transcription is performed converting 1 μg RNA to cDNA for each sample according to manufacturer's protocol (e.g., RT Kit, Applied Biosystems, Foster City, Calif.). Quantitative real-time polymerase chain reaction (PCR) is performed for gene expression analysis using 50 ng cDNA per sample. Gene expression assays for target genes and endogenous glyceraldehyde-3-phosphate dehydrogenase (GAPDH) control may be from, for example, Applied Biosystems. Expression is measured on a real-time PCR System 7500 (Applied Biosystems). Relative quantifications are calculated, for example, with SDS v.1.3.1 software.

5.6.3.3 Cytokine and Chemokine Protein Analysis

A 50 μl supernatant from each well is transferred into new round-bottomed 96 well plates and stored at −20° C. for cytokine analysis by cytometric bead array using a Luminex IS100 instrument (Luminex Corporation, Austin, Tex.). LincoPlex kits with antibody bound beads for Luminex xMAP Technology (Millipore) are combined into multiplex format prior to assay. Data analysis is performed using Upstate Beadview software. IL-2 and IFN-γ levels from SEB stimulated PBMC are measured by enzyme-linked immunoabsorbant assay (ELISA) (R&D Systems).

5.6.3.4 PMN Isolation and Stimulation

Polymorphonuclear cells (PMN) are isolated from human leukocytes by separation from PBMC using Ficoll gradient centrifugation to remove PBMC. Erythrocytes are removed by sedimentation in 3% dextran followed by hypotonic lysis in 0.2% saline. Finally, any contaminating monocytes are depleted using HLA class II magnetic beads. PMN ($3 \times 10^5$ cells/well) are pretreated with titrated compound for 1 hour, and then stimulated with Zymosan A particles (heat-killed *S cerevisiae*) at various doses. Polymyxin B sulfate (40 nM final) is added to all samples to neutralize any contaminating LPS. After overnight incubation, supernatants are harvested and assayed for IL-8 by ELISA.

For $LTB_4$ production, PMN are resuspended in phosphate-buffered saline without calcium or magnesium (BioWhittaker) containing 10 mM 4-(2-hydroxyethyl)-1-piperazineethanesulfonic acid (HEPES) (pH=7.2) and plated in 96-well tissue culture plates at a concentration of $1.7 \times 10^6$ cells/well. Cells are treated with 50 µM thimerosal (Sigma)/1 mM $CaCl_2$/1 mM $MgCl_2$ for 15 minutes at 37° C. 5% $CO_2$, then treated with compound in a final DMSO concentration of 0.01% in duplicate for 10 minutes. PMN are stimulated with 1 µM formyl-Met-Leu-Phe (fMLF, Sigma) for 30 minutes, then lysed by the addition of methanol (20% final concentration) and frozen in a dry ice/isopropanol bath for 10 minutes. Lysates are stored at −70° C. until the $LTB_4$ content is measured by competitive $LTB_4$ ELISA (R&D Systems).

For CD18/CD11b (Mac-1) expression, PMN are pretreated with compound for 10 minutes and stimulated with N-formyl-Met-Leu-Phe (fMLF) for 30 minutes, then placed on ice, stained with anti-CD18-FITC and anti-CD11b-PE and analysed by flow cytometry using a fluorescence-activated cell sorter (FACS) Calibur flow cytometer (BD Biosciences).

To measure adhesion of neutrophils to endothelial cells, human umbilical vein endothelial cells (HUVEC, Anthrogenesis Corporation, Cedar Knolls, N.J.) are plated out onto 96 well plates ($5 \times 10^3$ cells per well) in medium containing 2% FBS 4 days prior to the experiment to ensure adhesion of HUVEC to the plate. On the day of the experiment, neutrophils are isolated from human leukocytes and labeled with the fluorescent dye Calcein-AM (Molecular Probes, Oregon) for 1 hour. Labeled neutrophils ($2 \times 10^5$ per well) are added to the adhered HUVECs and pretreated with compound for 10 minutes at 37° C. in a humidified incubator at 5% $CO_2$. fMLF is added to trigger neutrophil adhesion to HUVECs for 30 minutes. The cells are washed with PBS containing 2% glucose to remove non-adherent neutrophils, and the number of adherent neutrophils was measured on a fluorimeter.

For IL-8 production assays, PMN are plated in 96-well tissue culture plates at $3 \times 10^5$ cells/well in complete medium, treated with compound in duplicate in a final DMSO concentration of 0.1% for 1 hour at 37° C. 5% $CO_2$. PMN are then stimulated with unopsonized, boiled Zymosan A (Sigma) at $2.5 \times 10^5$ particles/well for 18 hours. Supernatants are harvested and tested for IL-8 by ELISA (R&D Systems).

5.6.3.5 NK Cell Purification and Stimulation

NK cells are isolated from leukocyte units from healthy blood donors by 30-minute incubation with RossetteSep cocktail for NK cell enrichment by negative selection (StemCell Technologies, Inc.), followed by Ficoll-Hypaque density gradient centrifugation. $CD56^+$ NK cells are isolated to ~85% purity as determined by flow cytometry. Flat-bottom plates are coated with 100 µg/mL of human IgG (Sigma) overnight at 4° C. The unbound IgG is washed away. NK cells are plated at $2 \times 10^5$ cells/well into the 96-well plates, and 10 ng/mL of IL-2 (R&D Systems, Minneapolis Minn.) is added. Test compound is then added to the plate wells. After a 48-hour incubation, the supernatants are harvested and analysed for levels of TNF-α, IFN-γ, GM-CSF, and MIP-1α by ELISA (R&D Systems).

5.6.3.6 Keratinocyte Proliferation, TNF-α Production and Viability

For proliferation studies, human neonatal foreskin epidermal keratinocytes (HEKn cells) are obtained from Cell Applications, Inc. (San Diego, Calif.) and plated at 3000 cells/well in 96-well flat bottom tissue culture plates for two days. Cell proliferation is measured using the Cell Counting Kit (Dojindo Molecular Technologies, Inc, Gaithersburg, Md.). For TNF-α production and viability studies, HEKn cells are obtained from Cascade Biologics (Portland, Oreg.) and are grown in serum-free medium supplemented with growth factors. When cells reach 80% confluency, cells are trypsinized and plated at $1 \times 10^5$ cells/well in 6-well dishes. Plates are incubated for 24 hours to allow cell adhesion. HEKn cells are treated with test compound or 0.1% DMSO as the vehicle control for 1 hour before ultraviolet B (UVB) irradiation with 50 $mJ/cm^2$ in a UV Stratalinker 2400 (Stratagene, La Jolla, Calif.) calibrated with 312 nm UVB bulbs. Media and compounds are replaced, and cells are incubated for 18 hours. Supernatants are removed for testing in a TNF-α ELISA before 100 µl of adenosine triphosphate (ATP)-lite reagent (PerkinElmer Life and Analytical Sciences, Shelton, Conn.) is added to each well to assay for viability. Lysates are transferred to plates and shaken for 2 minutes before chemiluminescence is read on a TopCount NXT Luminescence Counter (PerkinElmer Life and Analytical Sciences).

5.6.4 Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by $^3H$-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of $^3H$-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

5.6.5 Cell Cycle Analysis

Cells are treated with DMSO or an amount of a compound provided herein overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.6.6 Apoptosis Analysis

Cells are treated with DMSO or an amount of a compound provided herein at various time points, then washed with annexin-V wash buffer (BD Biosciences). Cells are incubated with annexin-V binding protein and propidium iodide (BD Biosciences) for 10 minutes. Samples are analyzed using flow cytometry.

5.6.7 Anti-Proliferation Assay

Day 1: The cells are seeded to 96-well plate with 50 ul/well in 10% FBS RPMI (w/Glutamine, w/o pen-strip) for overnight. The following cells are used:

Colorectal cancer cell: Colo 205 3200 cells/well; positive control irinotecan

Pancreatic cancer cell: BXPC-3 1200 cells/well; positive control gemcitabine

Prostate cancer cell: PC3 1200 cells/well; positive control docetaxel

Breast cancer cell: MDA-MB-231 2400 cells/well; positive control paclitaxel

Day 2: The compounds are serially diluted from 0.00001 μm~10 μm (or 0.000001~1 μM) with 50 μl/well (of 2×) and added to the plates in duplicate with relative positive control. The plates were then incubated at 37° C. for 72 hours.

Day 5: The results are detected by CellTiter Glo method. 100 μl/well of CellTiter Glo reagent is added to the plates and incubated for 10 minutes at room temperature, and then analyzed on the Top Count reader. The $IC_{50}$ of each compound is typically based on the result of two or more individually experiments.

5.7 PDE 4 Inhibition

Abilities of certain compounds for inhibiting PDE 4 were determined using procedures substantially similar to those described in Sections 5.6.1 and 5.6.3, above.

The tested compounds included: (S)—N-(2-(1-(3-ethoxy-4-hydroxyphenyl)-2-(methylsulfonyl)ethyl)-3-oxoisoindolin-4-yl)cyclopropanecarboxamide; (S)—N-(2-(1-(3,4-dihydroxyphenyl)-2-(methylsulfonyl)ethyl)-3-oxoisoindolin-4-yl)cyclopropanecarboxamide; (S)—N-(2-(1-(3-hydroxy-4-methoxyphenyl)-2-(methylsulfonyl)ethyl)-3-oxoisoindolin-4-yl)cyclopropanecarboxamide; and 7-Amino-2-[(1S)-1-(3-ethoxy-4-methoxy-phenyl)-2-methanesulfonyl-ethyl]-2,3-dihydro-isoindol-1-one. From the tests, it was determined that $IC_{50}$ values of the tested compounds were in the range of about 2 to about 85 μM.

5.8 TNFα Inhibition

Abilities of certain compounds for inhibiting TNFα were determined using procedures substantially similar to those described in Section 5.6.2, above.

The tested compounds included: (2S,3S,4S,5R,6R)-6-(2-(2-((S)-1-(3-Ethoxy-4-methoxyphenyl)-2-(methylsulfonyl)ethyl)-1,3-dioxoisoindolin-4-ylamino)-2-oxoethoxy)-3,4,5-trihydroxytetrahydro-2H-pyran-2-carboxylic acid; (S)—N-(2-(1-(3-ethoxy-4-hydroxyphenyl)-2-(methylsulfonyl)ethyl)-3-oxoisoindolin-4-yl)cyclopropanecarboxamide; (S)—N-(2-(1-(3,4-dihydroxyphenyl)-2-(methylsulfonyl)ethyl)-3-oxoisoindolin-4-yl)cyclopropanecarboxamide; (S)—N-(2-(1-(3-hydroxy-4-methoxyphenyl)-2-(methylsulfonyl)ethyl)-3-oxoisoindolin-4-yl)cyclopropanecarboxamide; and 7-Amino-2-[(1S)-1-(3-ethoxy-4-methoxy-phenyl)-2-methanesulfonyl-ethyl]-2,3-dihydro-isoindol-1-one.

$IC_{50}$ values of the tested compounds were not determined, except for one test compound whose $IC_{50}$ was determined to be about 0.6 μM. For other test compounds, percent inhibition at 10 μM was determined. About 30 to about 45 percent inhibition of TNFα was observed when each of the compounds was present at 10 μM.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

All of the patents, patent applications and publications referred to herein are incorporated herein in their entireties. Citation or identification of any reference in this application is not an admission that such reference is available as prior art to this invention. The full scope of the invention is better understood with reference to the appended claims.

What is claimed is:

1. A pharmaceutical composition comprising a compound of formula (I):

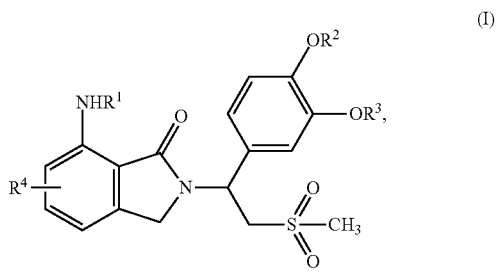

or a pharmaceutically acceptable salt, solvate, or stereoisomer thereof, wherein:

$R^1$ is glucuronide ("gluc"), or (cyclopropyl)-C(O)—, wherein the cyclopropyl may be substituted with one or more hydroxyl groups;

$R^2$ is hydrogen, methyl, or gluc;

$R^3$ is hydrogen, ethyl, or gluc; and $R^4$ is hydrogen, hydroxyl, or —O-gluc;

with the proviso that when $R^2$ is methyl and $R^3$ is ethyl, then $R^1$ cannot be unsubstituted (cyclopropyl)-C(O).

2. The composition of claim 1, wherein $R^1$ is (cyclopropyl)-C(O)—.

3. The composition of claim 1, wherein $R^2$ is hydrogen.

4. The composition of claim 1, wherein $R^2$ is methyl.

5. The composition of claim 1, wherein $R^2$ is gluc.

6. The composition of claim 1, wherein $R^3$ is hydrogen.

7. The composition of claim 1, wherein $R^3$ is ethyl.

8. The composition of claim 1, wherein $R^4$ is hydroxyl.

9. The composition of claim 1, wherein $R^4$ is —O-gluc.

10. A pharmaceutical composition comprising a compound having the structure:

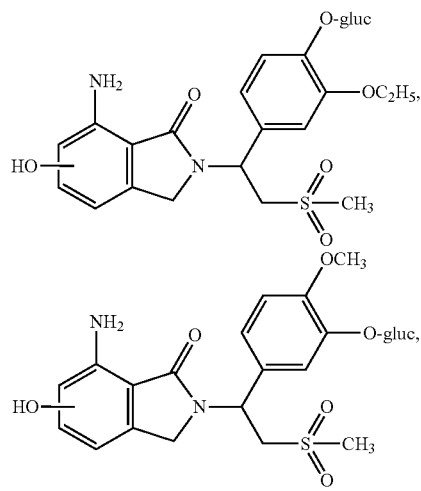

-continued

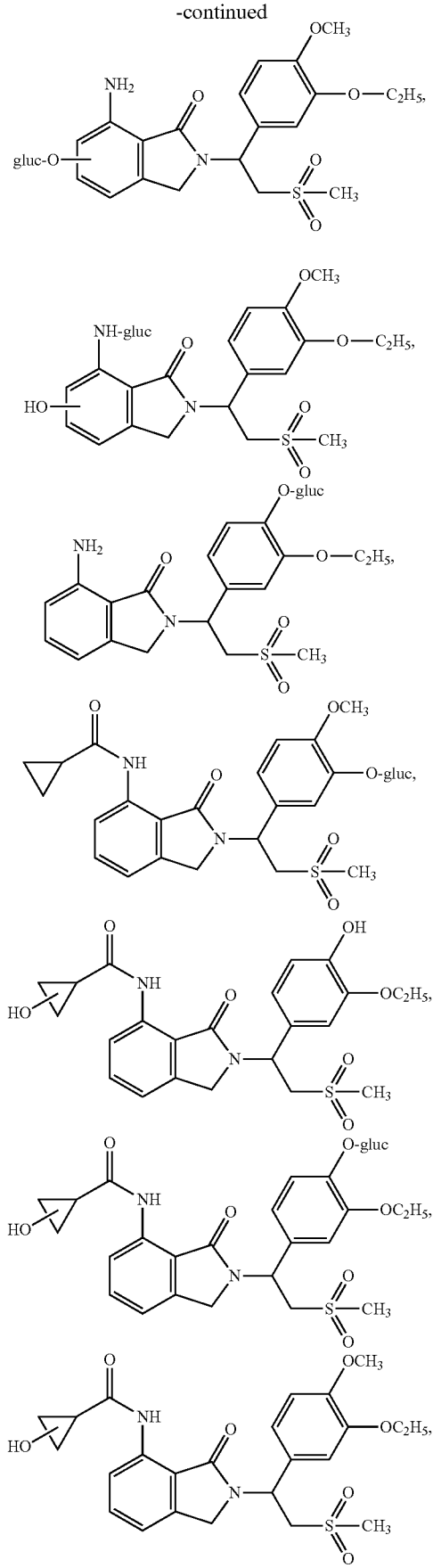

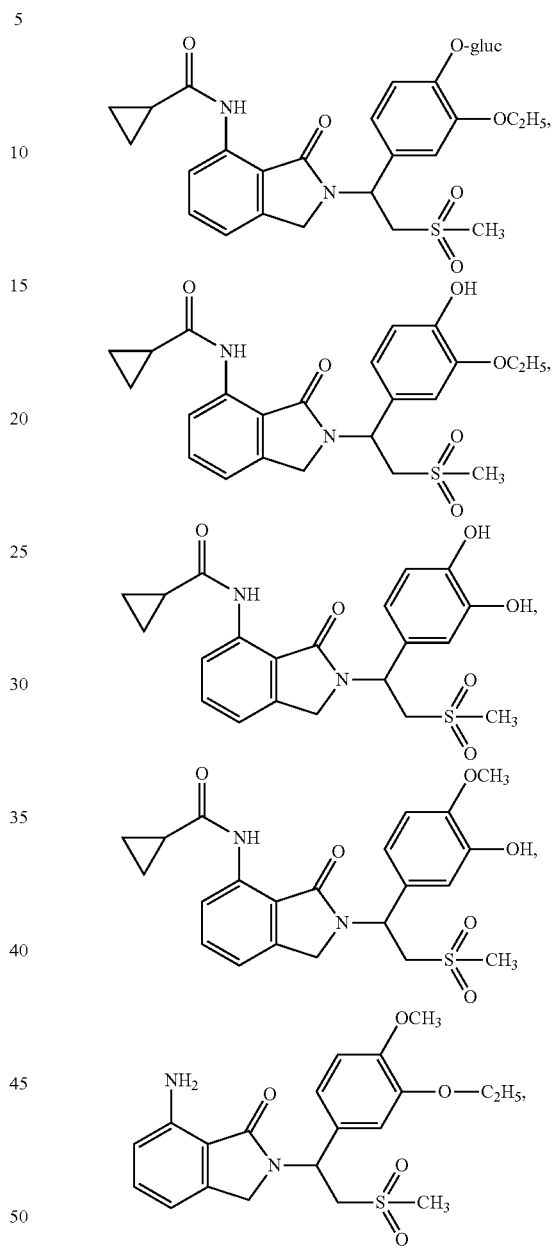

or a pharmaceutically acceptable salt, solvate, or stereoisomer thereof.

11. The composition of claim 1, wherein the compound is:

or a pharmaceutically acceptable salt, solvate, or stereoisomer thereof.

12. A method of treating or managing a disease or disorder comprising administering to a patient a composition of claim 1, or a pharmaceutically acceptable salt, solvate, or stereoisomer thereof, wherein the disease or disorder is cancer, pain, arthritis, Crohn's disease, 5q-deletion syndrome, sickle cell anemia, cachexia, adult respiratory distress syndrome, macular degeneration, Graft versus Host Reaction, chronic pulmonary inflammatory diseases, psoriatic arthritis, multiple sclerosis, systemic lupus erythromatosis, ENL in leprosy, psoriasis, fibrotic disease, oncogenic or cancerous conditions, asthma, chronic obstructive pulmonary disease, or atopic dermatitis.

13. A method of treating or managing a disease or disorder comprising administering to a patient a compound of claim 10, or a pharmaceutically acceptable salt, solvate, or stereoisomer thereof, wherein the disease or disorder is cancer, pain, arthritis, Crohn's disease, 5q-deletion syndrome, sickle cell anemia, cachexia, adult respiratory distress syndrome, macular degeneration, Graft versus Host Reaction, chronic pulmonary inflammatory diseases, psoriatic arthritis, multiple sclerosis, systemic lupus erythromatosis, ENL in leprosy, psoriasis, fibrotic disease, oncogenic or cancerous conditions, asthma, chronic obstructive pulmonary disease, or atopic dermatitis.

* * * * *

UNITED STATES PATENT AND TRADEMARK OFFICE
CERTIFICATE OF CORRECTION

PATENT NO. : 8,716,252 B2  
APPLICATION NO. : 13/518843  
DATED : May 6, 2014  
INVENTOR(S) : Schafer et al.

Page 1 of 1

It is certified that error appears in the above-identified patent and that said Letters Patent is hereby corrected as shown below:

IN THE CLAIMS:

In column 44, delete the following structure:

"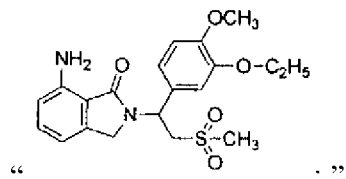."

Signed and Sealed this  
Eleventh Day of November, 2014

Michelle K. Lee  
*Deputy Director of the United States Patent and Trademark Office*